United States Patent
Ozawa et al.

(10) Patent No.: US 9,074,992 B2
(45) Date of Patent: Jul. 7, 2015

(54) X-RAY DIFFRACTION APPARATUS AND X-RAY DIFFRACTION MEASUREMENT METHOD

(75) Inventors: Tetsuya Ozawa, Hino (JP); Ryuji Matsuo, Hino (JP); Katsuhiko Inaba, Ome (JP)

(73) Assignee: RIGAKU CORPORATION, Akishima-Shi, Tokyo (JP)

( * ) Notice: Subject to any disclaimer, the term of this patent is extended or adjusted under 35 U.S.C. 154(b) by 735 days.

(21) Appl. No.: 13/311,228

(22) Filed: Dec. 5, 2011

(65) Prior Publication Data

US 2012/0140890 A1 Jun. 7, 2012

(30) Foreign Application Priority Data

Dec. 6, 2010 (JP) ................. 2010-271410

(51) Int. Cl.
*G01N 23/207* (2006.01)
*G01N 23/20* (2006.01)

(52) U.S. Cl.
CPC .................... *G01N 23/207* (2013.01)

(58) Field of Classification Search
CPC .... G01N 23/207; G01N 23/205; G01N 23/20
USPC ............................... 378/71, 74, 81
See application file for complete search history.

(56) References Cited

U.S. PATENT DOCUMENTS 7,158,609 B2 * 1/2007 Kikuchi et al. ............... 378/73
7,269,245 B2 * 9/2007 He et al. ..................... 378/71

FOREIGN PATENT DOCUMENTS

| JP | 9-145641 A | 6/1997 |
|----|------------|--------|
| JP | 09-304307 A | 11/1997 |
| JP | 2006-284210 A | 10/2006 |

OTHER PUBLICATIONS

Fewster, "Combining High-Resolution X-ray Diffractometry and Topography" Journal of Applied Crystallography, (1991), vol. 24, Part 2, pp. 178-183.
Lang et al., "Combining Optical Microscopy, X-ray Microradiography and X-ray Topography in the Study of Individual CVD Diamond Crystallites" Diamond and Related Materials, (1997), vol. 6, Issue 9, pp. 1226-1230.
Lorber et al., "Characterization of Protein and Virus Crystals by Quasi-planar wave X-ray Topography: a Comparison between Crystals Grown in Solution and in Agarose Gel" Journal of Crystal Growth, (1999), vol. 204, No. 3, pp. 357-368.
Search Report dated Jan. 19, 2012, issued in the corresponding German Patent Application No. 10 2011 087 537.9. (5 pages).

* cited by examiner

*Primary Examiner* — Irakli Kiknadze
(74) *Attorney, Agent, or Firm* — Buchanan Ingersoll & Rooney PC (57) ABSTRACT

There is provided an X-ray diffraction apparatus comprising an X-ray topography device for providing a spatial geometric correspondence to an X-ray exiting from a planar region of a sample to detect the X-ray as a planar X-ray topograph, and outputting the X-ray topograph as a signal; a two-dimensional imaging device for receiving a light-image of the planar region of the sample and outputting the light-image as a signal specified by planar positional information; and a video-synthesizing arithmetic control device for generating synthesized video data on the basis of an output signal from the X-ray topograph and an output signal from the imaging device.

16 Claims, 4 Drawing Sheets

X-RAY DIFFRACTION APPARATUS AND X-RAY DIFFRACTION MEASUREMENT METHOD

BACKGROUND OF THE INVENTION

1. Field of the Invention

The present invention relates to an X-ray diffraction apparatus and X-ray diffraction measurement method based on X-ray topography.

2. Description of the Related Art

X-ray topography has been known as one of X-ray diffraction measurement methods. X-ray topography is a measurement method devised so that a wide area of a sample is irradiated with X-rays, and the diffracted rays exiting the sample are detected in a plane (that is, in two dimensions) by an X-ray detector. Specifically, X-ray topography is a method in which diffracted rays that have exited from a planar region of a sample are provided with a spatial geometric correspondence and captured as a planar X-ray diffraction image. The planar X-ray diffraction image is called an X-ray topograph.

The form characteristics that appear in an X-ray topograph typically represent the compositional characteristics of an object. For example, lattice defects and lattice distortion in a single crystal appear as changes in the X-ray intensity in an X-ray topograph. For this reason, X-ray topography, which is a measuring method for obtaining an X-ray topograph, is at present widely used as a method for assessing the integrity of crystals in single crystal materials such as the Si (silicon) substrates in semiconductor devices.

There are also X-ray diffraction measurement methods in which a very small region of a sample is irradiated with a very thin X-ray, and a diverse range of measurements is performed on the very small region. Examples of such measurement methods include qualitative analysis, rocking curve measurement, reflectometry, reciprocal lattice mapping, in-plane measurement, and the like.

In conventional practice, method is used for evaluating the crystallinity of a single crystal in which X-ray topography and rocking curve measurement are performed using the same X-ray measuring device (for example, see patent reference 1). According to the evaluation method, a single crystal is examined for the presence of crystal defects by an X-ray topograph determined by X-ray topography, rocking curve measurement is performed only in the vicinity of the discovered defects, and the crystal defects are quantitatively measured. According to this evaluation method, the measurement time needed for the rocking curve measurement is considerably reduced in comparison with a case in which rocking curve measurement is performed over a wide area of a sample.

In conventional practice, X-ray single crystal evaluation devices are also used in which X-ray topography and X-ray diffraction measurement are performed selectively by switching the positions of appropriate optical elements in a single X-ray diffraction measuring device. The X-ray topography may be Lang method, section topography, surface reflection topography, reflection topography with a crystal monochromator, or the like, and the X-ray diffraction measurement performed in a limited field of measurement may be diffracted X-ray intensity absolute measurement, rocking curve measurement, diffraction profiling with a set analyzer crystal, or the like (for example, see patent reference 2).

PATENT REFERENCES

[Patent Reference 1] JP-A 9-145641
[Patent Reference 2] JP-A 2006-284210

SUMMARY OF THE INVENTION

According to the apparatus disclosed in patent reference 1, it is suggested that a section containing crystal defects in a single crystal be examined by X-ray topography and that rocking curve measurement be performed for the discovered section only. However, the position of the section where rocking curve measurements is to be performed has to be defined by methods that take time and are imprecise. In these methods, not only does the position of the section have to be clearly specified as a coordinate position in an X-ray topograph, which is a planar picture, but an X-ray that has passed through a pinhole collimator has to be doubly exposed on an X-ray topograph to confirm the position. For this reason, operations whereby a section having crystal defects determined by X-ray topography is set as a section to be measured using rocking curve analysis are extremely difficult and time-consuming operations.

A technique is disclosed for the apparatus disclosed in patent reference 2 whereby either a device for performing X-ray topography (that is, an X-ray topography device) or another X-ray measuring device is selectively set up as desired by switching the components or changing the arrangement position. However, the document does not touch upon the technological idea whereby the in-plane position of a crystal defect observable using an X-ray topograph is clearly specified with coordinates or the like.

Microscopy-based methods are also known as methods for discovering defects in the Si substrate of a semiconductor device. Specifically, if there is a lattice defect on the order of several micrometers, a designated area within the substrate is photographed by a reflective optical microscope, the photographic image is observed visually to search out crystal defects, and the in-plane positions of the defects are specified using coordinates or the like.

The methods using a reflective optical microscope have a problem, however, in that, while effective in cases in which the measurement object is an optically opaque substance, these methods cannot be applied to optically transparent substances. For example, an evaluation method using a reflective optical microscope cannot be applied to the transparent sapphire ($AL_2O_3$) substrates used in LEDs (Light Emitting Diodes).

Object of the Invention

An object of the present invention, which was designed in view of the problems with the conventional apparatuses, is to allow a position within in an in-plane region of an X-ray topograph to be clearly specifiable in an X-ray diffraction apparatus whereby an X-ray topograph related to a sample is determined by measurement.

Another object of the present invention is to provide an X-ray diffraction apparatus that is able to clearly specify a position in an in-plane region of a substance even when the substance is optically transparent, that is, has a high degree of optical clearness and cannot be observed using a reflective optical microscope.

Yet another object of the present invention is to provide an X-ray diffraction measurement method that allows an arbitrary position in an in-plane region of a transparent substance to be specified and subjected to an X-ray measurement.

Configuration of the Invention

The X-ray diffraction apparatus relating to the present invention comprises (1) X-ray topography means for providing a spatial geometric correspondence to an X-ray exiting from a planar region of a sample to detect the X-ray as a planar X-ray topograph, and outputting the X-ray topograph as a signal, (2) optical image-capturing means for receiving a light-image of the planar region of the sample and outputting the light-image as a signal specified by planar positional information, and (3) video synthesis means for generating synthesized video data on the basis of an output signal from the X-ray topograph and an output signal from the optical image-capturing means.

The optical image-capturing means in the above configuration may, for example, be an imaging device that uses a semiconductor imaging sensor, an optical microscope, or the like.

According to the present invention, transparent samples that cannot be made visible with the optical image-capturing means can be made visible by the X-ray topography means and used as a measurement object. Additionally, an arbitrary position in an in-plane region of a sample that has been made visible can be clearly specified by the video synthesis means. The specified positional information can be adapted as data for a diverse range of X-ray measurements subsequently performed on the sample.

In conventional X-ray diffraction apparatuses, the position in which an X-ray is incident on a sample had to be aligned with the region of interest by trial and error in a case in which the region of interest in an X-ray topograph was to be selected and an X-ray measurement performed. By contrast, according to the present invention, the subsequently performed X-ray measurement can be performed both quickly and accurately because the region of interest in an X-ray topograph can be clearly specified in a short timespan by the video synthesis means.

Figure 4A:
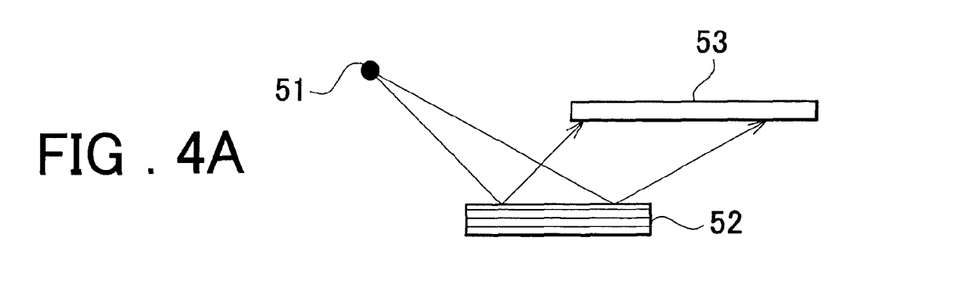
FIGS. 4A through 4D are diagrams showing examples of X-ray topography means that can be used for the X-ray diffraction apparatus relating to the present invention.

Any device can be used in the above configuration so long as the X-ray topography means is configured to allow a two-dimensional picture of a sample to be obtained. For example, the devices shown in FIGS. 4A through 4D can be used. The device shown in FIG. 4A is an X-ray topography device operating according to a divergent continuous X-ray method. In the device, continuous X-rays emitted from an X-ray point focal spot 51 strikes a sample 52, and an image of an X-ray topograph is captured by a two-dimensional X-ray detector 53.

Figure 4B:
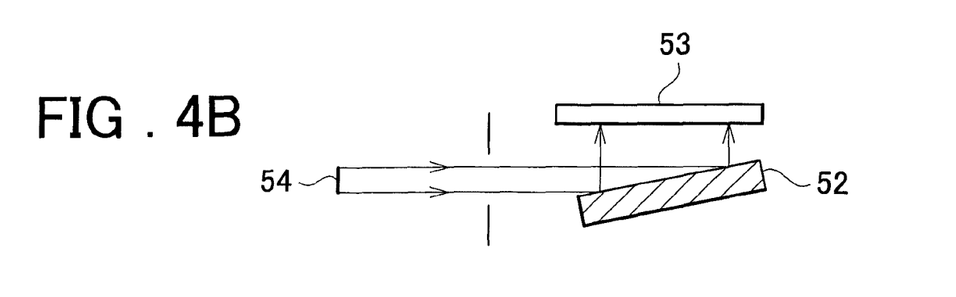

The device shown in FIG. 4B is an X-ray topography device operating according to the Berg-Barrett method, which uses reflection geometry created by a single-crystal method. In this device, a monochromatic X-ray emerging from a linear focal spot 54 strikes a sample 52, and an image of an X-ray topograph is captured by a two-dimensional X-ray detector 53.

Figure 4C:
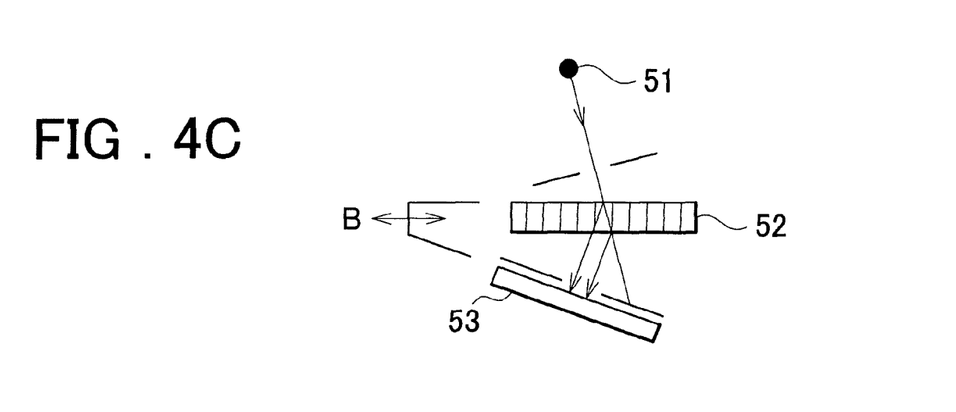

The device shown in FIG. 4C is an X-ray topography device operating according to the Lang method, which uses transmission geometry created by a single-crystal method. In the device, monochromatic X-rays emitted from a point focal spot 51 is converted to a linear shape by being passed through a strip-shaped slit, that is, a slit that is long in a vertical direction (that is, an up-down direction) to strike a sample 52, and an image of an X-ray topograph is captured by a two-dimensional X-ray detector 53. The sample 52 and the X-ray detector 53 jointly perform a translational movement as indicated by the arrows B.

Figure 4D:
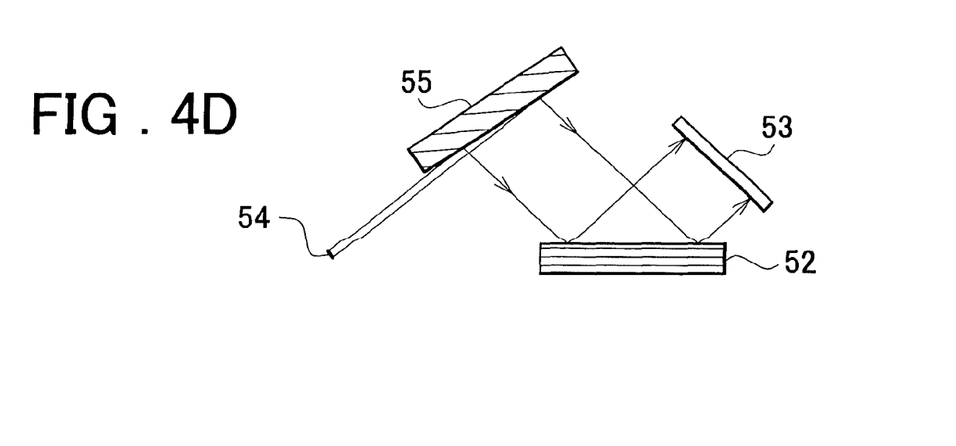

The device shown in FIG. 4D is an X-ray topography device based on a double-crystal method. In this device, monochromatic X-rays emitted from a linear focal spot 54 is asymmetrically reflected by a first crystal 55, and is then caused to strike a sample 53, which is a second crystal, and an image of an X-ray topograph is captured by a two-dimensional X-ray detector 53.

Further, in each of the aforementioned devices, the X-ray detector is not limited to being a two-dimensional X-ray detector, but may also be a one-dimensional X-ray detector or a zero-dimensional X-ray detector, as long as the X-ray detector is able to obtain a two-dimensional picture of a sample.

In the X-ray diffraction apparatus relating to the present invention, the video synthesis means is able to generate the synthesized video data on the basis of a reference position set for the sample. This configuration makes it possible to accurately align an X-ray topograph and a light-image of a sample.

The reference position can be an edge of the sample or a mark provided to the sample. In a case in which the sample is a transparent substance or a substance having the high degree of clearness, an optical image-capturing means such as an optical microscope or the like cannot provide visual confirmation of the structure of the sample interior. On the other hand, the external peripheral edge of the sample can be visually confirmed, because conditions of visible light for transmission, reflection and scattering against the sample interior are not identical with conditions of visible light for transmission, reflection and scattering against air. For this reason, the edge can be set as the reference for the video matching process.

In the X-ray diffraction apparatus relating to the present invention, the optical image-capturing means may be configured having a semiconductor image sensor in which a plurality of semiconductor X-ray light-receiving elements are lined up in a planar or linear formation. The X-ray light-receiving elements may, for example, be CCDs (Charge Coupled Devices), CMOSs (Complementary Metal Oxide Semiconductors), or so-called photon counting elements, which are components for receiving an X-ray and directly outputting an electric signal. It is preferable for the optical image-capturing means to capture a light-image of an entire sample, and a semiconductor image sensor is ideal in this sense.

In the X-ray diffraction apparatus relating to the present invention, the sample is preferably an optically transparent single crystal substance, surface of which reflects light of small amount. With optical image-capturing means such as imaging devices and the like, transparent substances cannot be used as observation objects, but the X-ray diffraction apparatus of the present invention makes a transparent substance visible as an X-ray topograph, and can therefore make a transparent substance into an observation object. Additionally, each position within an in-plane region of the substance can be specified in the form of coordinate information such as planar coordinates or the like by the video synthesis means.

The X-ray diffraction apparatus relating to the present invention may further comprise (1) an X-ray measurement system for irradiating the sample with an X-ray within a narrower region than the region in which the sample is irradiated with an X-ray in the X-ray topography means, and detecting an X-ray exiting from the sample at this time, and (2) sample moving means for causing the sample to perform a translational movement.

With this configuration, the region of interest can be moved to the X-ray irradiated region to perform detailed X-ray measurement in a case in which, for example, an X-ray topograph is observed and a region of interest such as a lattice defect or the like is specified.

Such an X-ray measurement system may, for example, be at least one of a rocking curve measuring device, a reflectometry device, a reciprocal lattice mapping device, an in-plane measuring device, and an X-ray powder diffraction apparatus.

In the X-ray diffraction apparatus relating to the present invention, the X-ray topography means and the X-ray measurement system preferably have a common X-ray source. This makes it possible to avoid circumstances in which a sample must be changed in its position when respective measurements are performed, to reduce the cost, to use a narrower space for installing the apparatus, and to allow the X-ray source to be controlled in a simple manner.

The X-ray diffraction measurement method relating to the present invention is an X-ray diffraction measurement method for performing a measurement using an X-ray diffraction apparatus configured as described above, the method comprising: (1) determining the presence of a crystal defect on the basis of an output result from the X-ray topography means, (2) specifying the position of the crystal defect by the planar positional information on the basis of the synthesized video data determined by the video synthesis means, (3) moving the sample by the sample moving means on the basis of the specified planar positional information, and causing the crystal defect to move to an X-ray irradiation position in the X-ray measurement system, and (4) performing measurement by the X-ray measurement system.

Effect of the Invention

According to the X-ray diffraction apparatus of the present invention, a transparent sample that cannot be made visible with an optical image-capturing means such as an optical microscope or the like can be made visible by an X-ray topography means and made into a measurement object. Additionally, an arbitrary position in an in-plane region of a sample that has been made visible can be clearly specified by a video synthesis means. The specified positional information can be adapted as data for a diverse range of X-ray measurements subsequently performed on the sample.

In conventional X-ray diffraction apparatuses, the position in which an X-ray is incident on a sample had to be aligned with the region of interest by trial and error in a case in which the region of interest in an X-ray topograph was to be set and an X-ray measurement performed. By contrast, according to the present invention, the subsequently performed X-ray measurement can be performed both quickly and accurately because the region of interest in an X-ray topograph can be clearly specified in a short timespan by the video synthesis means.

According to the X-ray diffraction measurement method of the present invention, a transparent substance can be made visible by an X-ray topograph, and X-ray measurement can be performed once the arbitrary position of interest in the in-plane region of the X-ray topograph has been clearly set by coordinates or the like.

DESCRIPTION OF THE PREFERRED EMBODIMENTS

The following is an explanation, made on the basis of an embodiment, of the X-ray diffraction apparatus and the X-ray diffraction measurement method relating to the present invention. It is apparent that the present invention is not restricted to the embodiment. The explanation from here on refers to the drawings, but the drawings sometimes show constituent components at a scale that is different from the actual proportions in order to make feature-specific sections easier to understand.

Figure 1:
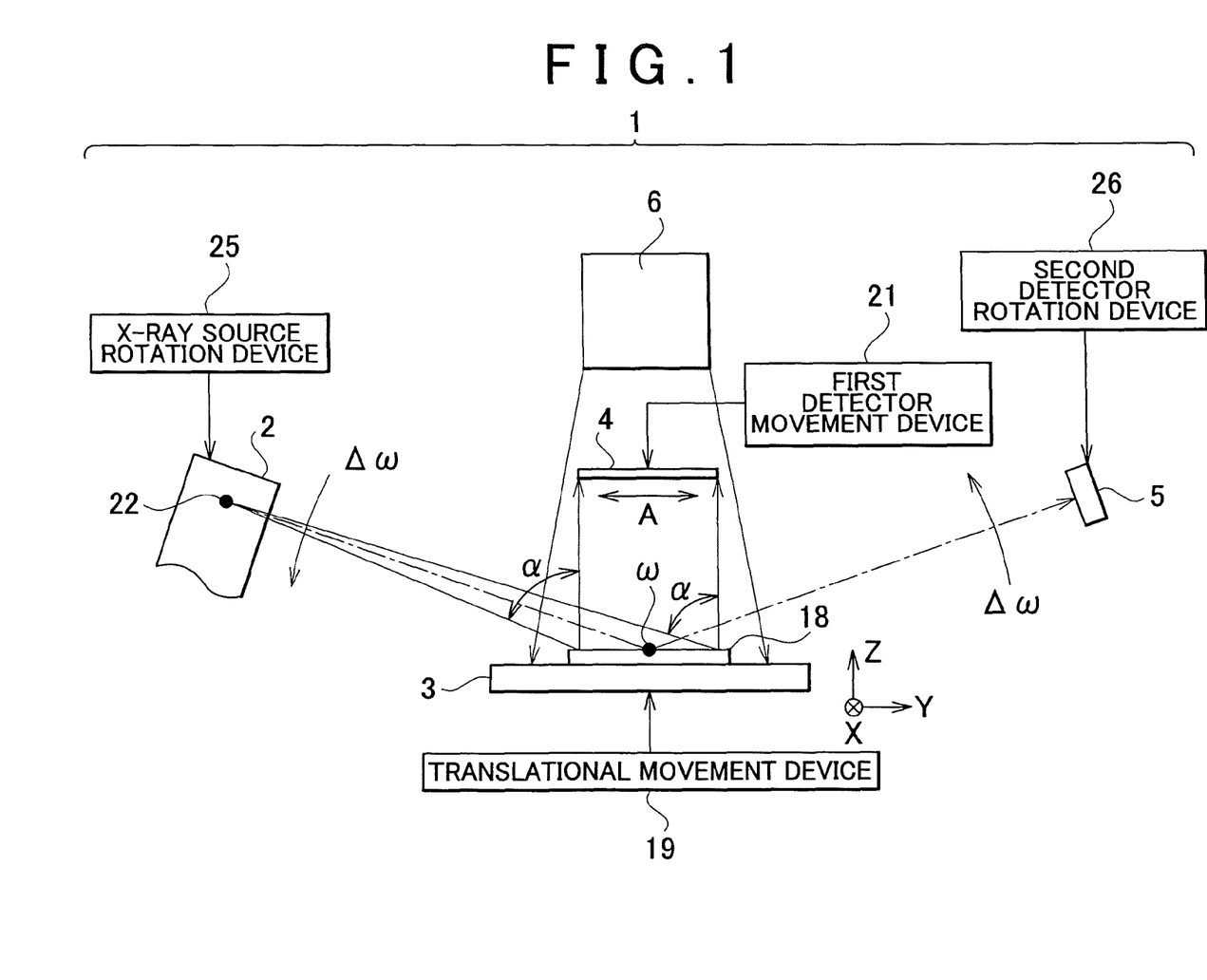
FIG. 1 is a diagram showing an embodiment of the X-ray diffraction apparatus relating to the present invention.
Figure 2:
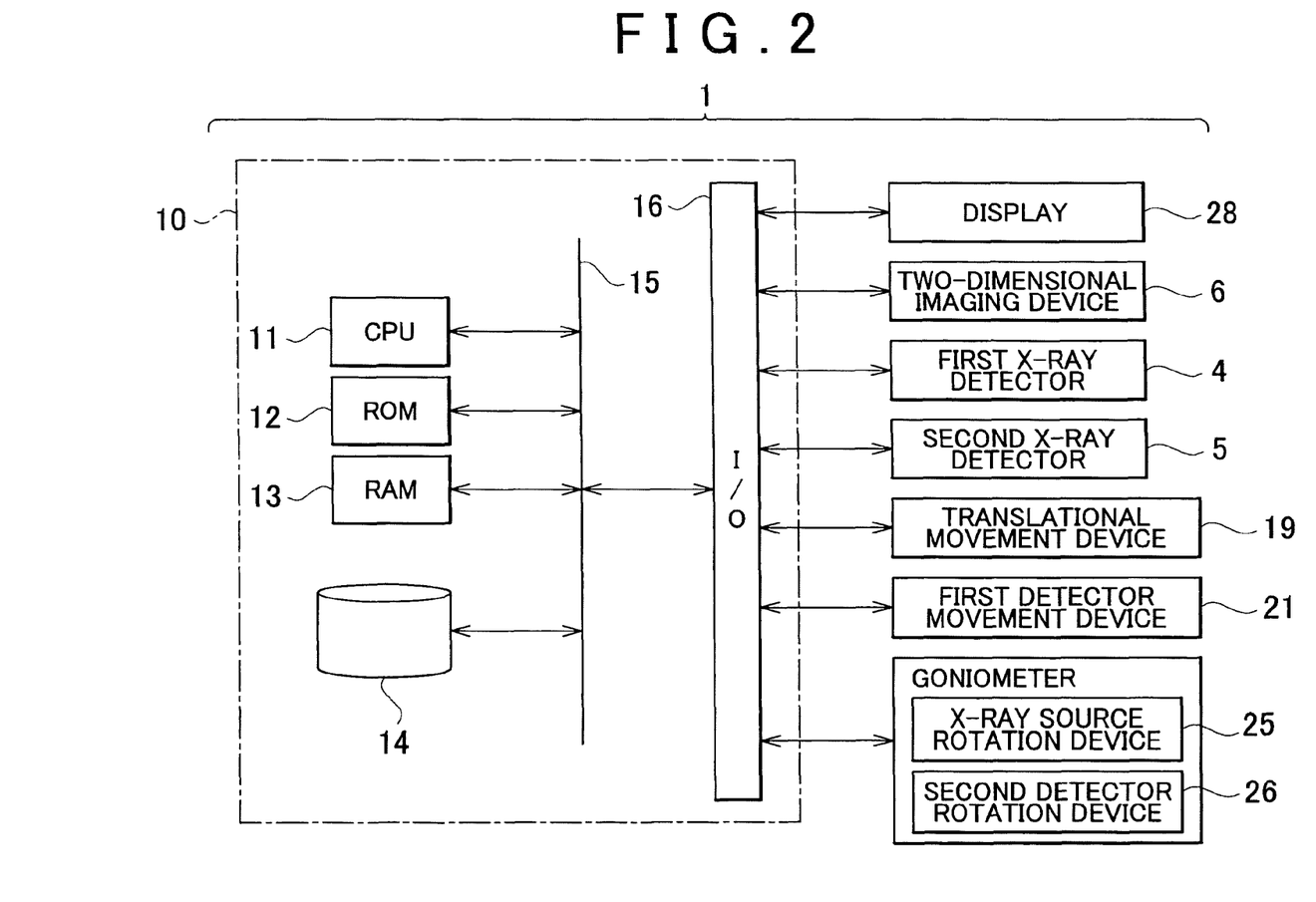
FIG. 2 is a block diagram showing an example of the control section of the X-ray diffraction apparatus in FIG. 1.

FIG. 1 shows a mechanical section of an embodiment of the X-ray diffraction apparatus relating to the present invention. FIG. 2 shows an electric control panel of the present embodiment. In FIG. 1, an X-ray diffraction apparatus 1 has an X-ray tube 2, a sample mount 3, a first X-ray detector 4, a second X-ray detector 5, and a two-dimensional imaging device 6, which is an optical image-capturing means. In FIG. 2, the X-ray diffraction apparatus 1 has a control device 10. The control device 10 is configured by a computer comprising the following elements, which are connected by a bus 15: a CPU (Central Processing Unit) 11, a ROM (Read Only Memory) 12, a RAM (Random Access Memory) 13, and a memory 14. The bus 15 includes a program bus and a data bus.

The sample mount 3 in FIG. 1 is a mount for loading a sample 18, which is a measurement object. The sample mount 3 in the present embodiment is a mount whose surface for loading the sample 18 is a horizontal plane. A support member for supporting the sample 18 may also be used instead of the sample mount 3. A translational movement device 19 is attached to the sample mount 3. The translational movement device 19 causes the sample 3 to perform a translational movement over an arbitrary distance in an X-Y plane. Specifically, the sample mount 3 is an X-Y stage that performs translational movement in a plane. The translational movement device 19 is linked to the control device 10 via an input/output interface 16 in FIG. 2.

Further, the X-direction in FIG. 1 is a direction that goes through the paper surface in FIG. 1, the Y-direction is a right-left direction (that is, a direction that is orthogonal to the X direction), and the X-Y plane is a surface that includes both a line showing the X direction and a line showing the Y-direction. The X-Y plane is a surface that is orthogonal to the paper surface in FIG. 1 and is a horizontal surface in the present embodiment.

Assuming that the direction orthogonal both to the X-direction and to the Y-direction is a Z-direction, the Z-direction is a direction parallel to the paper surface in FIG. 1 and is a vertical direction in the case of the present embodiment. The X-ray diffraction apparatus 1 may optionally have a device for causing the sample mount 3 to perform a translational movement in the Z-direction.

In the case of the present embodiment, the sample 18 is a sapphire substrate used as an LED (Light Emitting Diode) substrate. The sapphire substrate is a transparent single crystal substrate. Because the electrical characteristics of an LED depend greatly on whether or not the LED substrate has crystal defects, it is important to check for the presence of crystal defects. The inspection method for crystal defects is stated in the following.

The first X-ray detector 4 is formed by a semiconductor image sensor. Specifically, the first X-ray detector 4 is configured with a two-dimensional pixel-type X-ray detector comprising a plurality of X-ray light-receiving semiconductor pixels (picture elements) lined up in two dimensions (that is, in a plane) within the X-Y plane. The number of pixels may, for example, be 512×512 (height×width). The semiconductor pixels may be CCDs (Charge Coupled Devices), CMOS's (Complementary Metal Oxide Semiconductors), or so-called photon counting elements, which are components for receiving an X-ray and directly outputting an electrical signal.

The first X-ray sensor 4 can also be an imaging plate (IP). An IP is a plate having the property of storing up energy when irradiated with X-rays, that is, is a plate-shaped substance. The first X-ray detector 4 is provided so as to be substantially parallel to the sample-loading surface of the sample mount 3. An output terminal of the first X-ray detector 4 is linked to the control device 10 via the input/output interface 16 in FIG. 2.

In FIG. 1, a first detector movement device 21 is attached to the first X-ray detector 4. The first detector movement device 21 causes the first X-ray detector 4 to move substantially parallel to the sample-loading surface of the sample mount 3, as shown by the arrows A. The translational movement is designed to allow the first X-ray detector 4 to receive an X-ray that exits the sample 18 at an angle α. The first detector movement device 21 can be configured using a translational movement mechanism that includes a threaded shaft such as a ball screw or the like, for example. The first detector movement device 21 is linked to the control device 10 via the input/output interface 16 in FIG. 2.

The X-ray tube 2 in FIG. 1 has an X-ray focus 22, which is an X-ray source. A cathode (not shown) and an anticathode (not shown) are disposed in the interior of the X-ray tube 2. The region where the electrons discharged from the cathode impact the surface of the anticathode is the X-ray focus 22, and X-rays radiate from the X-ray focus 22. In the present embodiment, an X-ray topography device operating according to the continuous emission X-ray method shown in FIG. 4A is used, a continuous X-ray with a spot focal point is taken out from the X-ray focus 22, and the X-ray irradiates the sample 18 in a plane. At this time, an X-ray emerging in a plane from the sample 18 is received by the first X-ray detector 4, and, for example, a planar X-ray diffraction image 23, that is, an X-ray topograph, such as the one exemplified schematically in FIG. 3B is obtained. Specifically, the X-ray topography means in the present embodiment is configured using the X-ray focus 22 and the first X-ray detector 4 in FIG. 1.

The second X-ray detector 5 is formed by a semiconductor image sensor in the same manner as the first X-ray detector 4. Specifically, the second X-ray detector 5 is configured with a two-dimensional pixel-type X-ray detector comprising a plurality of X-ray light-receiving semiconductor pixels (picture elements) lined up in two dimensions (that is, in a plane) within the X-Y plane. The number of pixels may, for example, be 512×512 (height×width). The semiconductor pixels may be CCDs (Charge Coupled Devices), CMOS's (Complementary Metal Oxide Semiconductors), or so-called photon counting elements, which are components for receiving an X-ray and directly outputting an electrical signal. An output terminal of the second X-ray detector 5 is linked to the control device 10 via the input/output interface 16 in FIG. 2.

A ray source rotation device 25 is attached to the X-ray tube 2 in FIG. 1. A second detector rotation device 26 is attached to the second X-ray detector 5. The ray source rotation device 25 causes the X-ray focus 22 to rotatably move about an axis ω passing through a surface corresponding to the surface of the sample 18. The axis ω is a line that extends through the paper surface in FIG. 1 at a right angle. The second detector rotation device 26 causes the second X-ray detector 5 to rotatably move about the axis ω.

The ray source rotation device 25 and the second detector rotation device 26 are respectively configured using an appropriate rotational drive device. The device may, for example, be configured using a mechanism for transmitting the rotational drive power of a servo motor, pulse motor, or other motor with a controllable angle of rotation to the X-ray tube 2 and the second X-ray detector using a drive transmission mechanism or other drive power transmission device comprising a worm or a worm wheel.

The ray source rotation device 25 controls, that is, measures, the angle of the X-ray focus 22 with respect to the sample 18. The second detector rotation device 26 controls, that is, measures, the angle of the second X-ray detector 5 with respect to the sample 18. Specifically, the ray source rotation device 25 and the second detector rotation device 26 operate in tandem and constitute an angle-measuring instrument, that is, a goniometer, for measuring the respective angles of the X-ray focus 22 and the second X-ray detector 5 with respect to the sample 18. The goniometer is linked to the control device 10 via the input/output interface 16 in FIG. 2.

The two-dimensional imaging device 6 in FIG. 1 may, for example, be configured by an illumination device for illuminating the sample 18, and a two-dimensional CCD image sensor for receiving the light-image of the sample 18 and generating a corresponding electrical signal. The illumination device and CCD image sensor components are not shown in the drawings. The illumination device is unnecessary in a case in which the surroundings are sufficiently bright. It is apparent that the two-dimensional imaging device 6 can have a different configuration as needed.

Figure 3A:
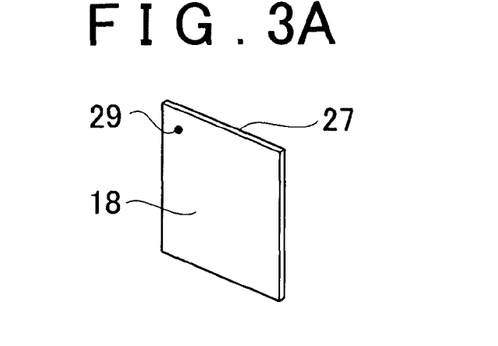
FIGS. 3A through 3D are diagrams for explaining video processing performed by the control section in FIG. 2.
Figure 3B:
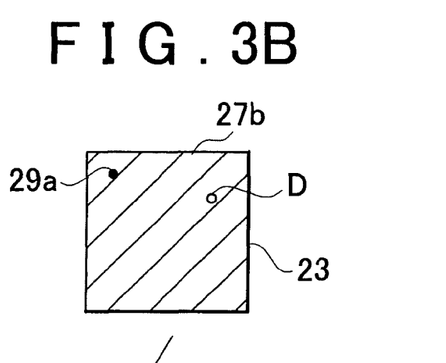
Figure 3C:
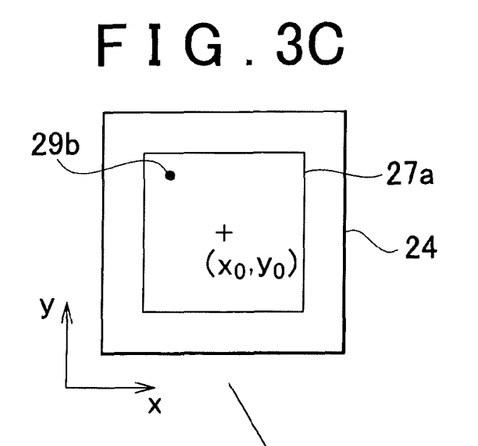

The two-dimensional imaging device 6 acquires a planar optical image 24 such as the one schematically exemplified in FIG. 3C, for example. Because the sample 18 in the present embodiment is a sapphire substrate, which is a transparent substance, a light-image 27a made to correspond to the edge 27 of the external periphery can be visually confirmed, but the internal structure cannot be captured as an optical image. However, the two-dimensional imaging device 6 can specify an arbitrary point in an in-plane region that includes the sample 18 by using XY coordinates, that is, two-dimensional coordinates. For example, a point where the sample 18 is irradiated with a direct beam from the X-ray focus 22 in FIG. 1, that is, a point where the sample 18 intersects with the X-ray optical axis, can be specified, for example, as the coordinate values $(x_0, y_0)$. The two-dimensional imaging device 6 is linked to the control device 10 via the input/output interface 16 in FIG. 2.

As a video display device, a display 28 is linked to the control device 10 via the input/output interface 16. A driver for generating a video signal corresponding to an optical image and a driver for generating a video signal corresponding to an X-ray topograph are installed in the memory 14. The topograph picture 23 shown in FIG. 3B and the optical image 24 shown in FIG. 3C can be displayed on the screen of the display 28 in FIG. 2 by the functioning of the drivers thereof.

The operation of the X-ray diffraction apparatus 1 thus configured is described below.

(Preparing the Sample)

First, as shown in FIG. 3A, a mark 29 that can be captured as a picture using both an X-ray and light is attached at an appropriate location of a sapphire substrate, which is the sample 18. In the present embodiment, the appropriate location is a corner. The sample 18 is then loaded on the sample mount 3 in FIG. 1.

(Photographing an X-Ray Topograph)

Next, the X-ray tube 2 is rotatably moved to a designated position, and the X-ray focus 22 is disposed at a designated angular position with respect to the sample 18 so that a diffracted ray will be obtained from the sample 18. The corresponding angle of the X-ray taken in by the X-ray detection surface of the first X-ray detector 4 is set to a with respect to the incident X-ray. In this state, the sample 18 is irradiated with an X-ray, an X-ray exiting the sample 18 is detected by the first X-ray detector 4, and a two-dimensional picture, that is, an X-ray topograph 23 such as the one shown in FIG. 3B, is obtained. The picture provides pixel-size resolution for the positions irradiated by the X-ray, and displays the intensity of the X-ray at the respective positions.

When the internal structure of the sample 18 is uniform, the intensity of the X-ray is uniform, but because a diffraction condition is not satisfied when there are lattice defects in the sample 18, the corresponding section appears as a color-displaying pattern in the X-ray topograph. Examples of such patterns include monochromatic gray patterns wherein the concentration differs in accordance with the magnitude of the X-ray intensity, and patterns wherein hue (a color classification such as red, yellow, green, and the like) differs in accordance with the magnitude of the X-ray intensity. The same occurs when an LED device is formed on the sample 18. If it is assumed, for example, that the presence of a lattice defect is discovered at a location marked by a symbol D, then, because the sample 18 has the mark 29 on the corner, a corresponding X-ray mark-image 29a will also appear in a corner of the X-ray topograph.

Because the X-ray topograph 23 is a planar picture determined by a plurality of pixels, the mutual position of each point in the X-ray topograph 23 can be decided based on the positional information of each of the pixels. However, the absolute position of the entire X-ray topograph 23 cannot be determined. Accordingly, even if the defect D is observed, the absolute coordinate position cannot be accurately understood.

(Photographing a Planar Light-Image of the Sample)

The two-dimensional imaging device 6 in FIG. 1 photographs the sample 18 and the periphery thereof either concurrently, or with an appropriate time difference as needed, relative to the photographing of the X-ray topograph. At this time, the first X-ray detector 4 may be removed from the field of vision of the two-dimensional imaging device 6 as needed. The two-dimensional imaging device 6 may, for example, produce an image such as the one shown in FIG. 3C. Because the sample 18 is optically transparent, the light-image 27a corresponding to the external peripheral edge cannot be separated and a light-image corresponding to the internal structure of the sample 18 cannot be captured by the two-dimensional imaging device 6. However, a light-image 29b of the mark 29 attached to the sample 18 can be captured.

The position of the optical image 24 with respect to the incident X-ray in FIG. 1 can be clearly resolved using XY coordinates. For example, the incident position of a direct beam, that is, the position intersecting with the optical axis of an incident X-ray, can be specified as coordinate values ($x_0$, $y_0$).

(Video Processing)

The CPU 11 in FIG. 2 performs an arithmetic operation to combine, or synthesize, the X-ray topograph 23 and the optical image 24 according to software stored in the memory 14. Specifically, the CPU 11 specifies the coordinate position of the X-ray mark image 29a in the X-ray topograph 23 in topograph coordinates, specifies the coordinate position of the light mark light-image 29b in the optical image 24 in XY coordinates, and converts the coordinate values of the entire X-ray topograph 23 so that both coordinate positions overlap in the XY coordinates of the optical image 24.

Figure 3D:
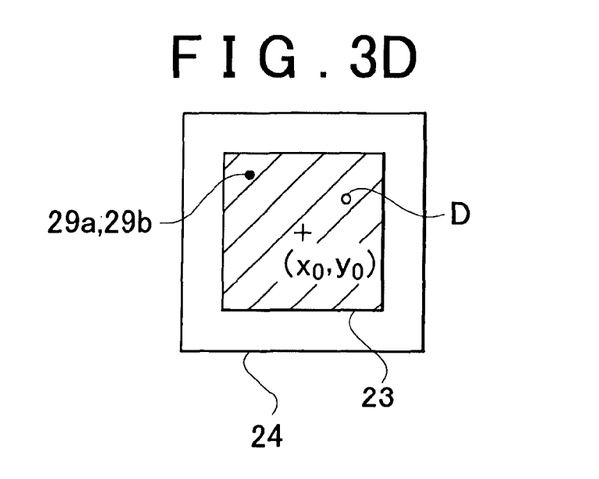

The conversion determines a picture wherein the optical image 24 and the X-ray topograph 23 overlap each other at the mark images 29a, 29b, as shown in FIG. 3D. The video data of the synthesized image is transmitted to the video display controller of the display 28 in FIG. 2 as needed, and displayed on the screen of the display 28.

(Rocking Curve Measurement)

The measurement operator can visually confirm the presence of a defect D in the X-ray topograph 23 by observing the screen in FIG. 3D. The measurement operator may sometimes want to set the defect D as an ROI (region of interest, or object region) and ascertain the detailed structure of the region. For example, the operator may want to subject the region in the vicinity of the defect D to rocking curve measurement and obtain quantitative information.

In this case, the measurement operator inputs the position of the defect D using a mouse pointer, touch panel, or the like on the screen of the display 28 in FIG. 2, or by manipulating a keyboard. The CPU 11 actuates the translational movement device 19, causes the sample 18 loaded on the sample mount 3 to perform a translational movement, and causes the sample 18 to perform the translational movement so that the area of the defect D coincides with the position ($x_0$, $y_0$) of the X-ray optical axis.

In FIG. 3D, an instruction causing the defect D to move to the position ($x_0$, $y_0$) can be issued by a so-called drag-and-drop operation in which the mouse is manipulated to move the defect D to the position ($x_0$, $y_0$). In the process, the X-ray topograph image 23 on the screen of the display 28 can also be moved along the screen in concert with the drag-and-drop manipulation.

Next, the measurement operator sets a state in which a very narrow monochromatic X-ray beam can irradiate the defect D in the sample 18 and the vicinity of the defect by inserting a pinhole collimator in the optical axis of the incident X-ray in FIG. 1, and performs rocking curve measurement. Specifically, in a state in which the sample 18 is immovably fixed in position, the X-ray focus 22 and the second X-ray detector 5 are rotatably moved in mutual synchrony about an axis $\omega$ in the same direction, as shown by the arrows $\Delta\omega$, and at the same designated angular speed to an angular position in which a diffracted ray can be obtained, and changes in the intensity of the diffracted ray are measured at each angular position. A known rocking curve can thereby be determined, and the defect D in the sample 18 can be quantitatively known based on the peak intensity, half width, diffraction angle, and the like of the rocking curve.

According to the present embodiment, a transparent sample 18 that cannot be made visible by the two-dimensional imaging device 6 can thus be made visible by the X-ray topography means (X-ray focus 22, first X-ray detector 4, or the like), that is, by displaying colors according to display conditions, whereby an ROI can be set based on an image that has been made visible, the optical image from the two-dimensional imaging device 6 and the X-ray topograph from the X-ray topography means can be combined together, and accurate XY coordinates can be specified for the ROI.

A coordinate-specified ROI can thus be measured using a desired dedicated measuring system such as a rocking curve measuring device or the like. Aligning an ROI with the measurement position of a dedicated measuring system by trial and error, as in conventional practice, requires a long time for the adjustments and sometimes makes it impossible to accurately specify the desired ROI, whereas the present embodiment allows such problem to be overcome, an ROI to be accurately specified in a short time, and X-ray measurement to be carried out.

Other Embodiments

The present invention is described above with reference to a preferred embodiment, but the present invention is not limited to this embodiment and may be altered in various ways within the scope of the invention described in the claims.

For example, an X-ray topography device operating according to the continuous emission X-ray method shown in FIG. 4A is used as the X-ray topography means in the aforementioned embodiment, but an X-ray topography device of another configuration such as the one shown in FIG. 4B, 4C, or 4D can be used instead. An X-ray topography device of yet another configuration (not shown) can also be used.

An arbitrary configuration other than the aforementioned configuration can be employed as needed for the two-dimensional imaging device 6. In the aforementioned embodiment, a sapphire single crystal, which is a transparent substance, was applied as the sample 18, but it is apparent that an opaque substance can also be used as the measurement object.

Because the surface of the sample 18 and the X-ray receiving surface of the first X-ray detector 4 may not be in parallel relation with each other, measurement images of X-ray topograph may be recorder in a condition where width of the image is distorted (see FIGS. 4B, 4C, 4D). In this case, an X-ray topograph 23 and an optical image 24 are synthesized with use of both the external peripheral profile of the sample 18 and a mark image 29a to be processed in synthesizing operation.

Even when the external peripheral profile of the sample 18 is larger than the field of vision of the optical image 24, by providing three or more marks 29 on appropriate positions in the sample 18, the X-ray topograph 23 and the optical image 24 can be synthesized with each other to be processed in synthesizing operation.

Marks 29 may be formed of anticorrosive paint including ferriferous oxided substances, and the like. Marks 29 may also be preferably formed of pieces of aluminum equipped with an adhesive tape on one side thereof, which can be easily removable.

When measuring many samples of the same quality, compensation of distortion between the X-ray topograph image and the optical image is carried out for an initial one sample. For samples successively measured, one point on the outer peripheral surface of the sample is set to one reference mark, and then measurement for the sample is carried out.

In the above embodiment, a mark 29 showing the reference position in FIG. 3A is provided to the sample 18, and the X-ray topograph 23 and the optical image 24 are synthesized using the mark 29 as a reference. However, instead of this method, the X-ray topograph 23 and the optical image 24 can also be synthesized using, as a reference, a light-image 27a corresponding to the external peripheral edge 27 of the sample 18 (FIG. 3C) and the image 27b of the external peripheral edge of the X-ray topograph (FIG. 3B).

What is claimed is:

1. An X-ray diffraction apparatus comprising:
   X-ray topography means for providing a spatial geometric correspondence to an X-ray exiting from a planar region of a sample to detect the X-ray as a planar X-ray topograph, and outputting the X-ray topograph as a signal;
   optical image-capturing means for receiving a light-image of the planar region of the sample and outputting the light-image as a signal specified by planar positional information; and
   video synthesis means for generating synthesized video data on the basis of an output signal from the X-ray topopgraphy means and an output signal from the optical image-capturing means.

2. The X-ray diffraction apparatus according to claim 1, wherein
   the video synthesis means generates the synthesized video data on the basis of a reference position set for the sample.

3. The X-ray diffraction apparatus according to claim 2, wherein
   the reference position is an edge of the sample or a mark provided to the sample.

4. The X-ray diffraction apparatus according to claim 3, wherein
   the X-ray topography means has a semiconductor image sensor in which a plurality of semiconductor X-ray light-receiving circuit elements are lined up in a planar or linear formation.

5. The X-ray diffraction apparatus according to claim 4, wherein
   the sample is an optically transparent single crystal substance, surface of which reflects light of small amount.

6. The X-ray diffraction apparatus according to claim 5, further comprising:
   an X-ray measurement system for irradiating the sample with an X-ray within a narrower region than the region in which the sample is irradiated with an X-ray in the X-ray topography means, and detecting an X-ray exiting from the sample at this time; and
   sample moving means for causing the sample to perform a translational movement.

7. The X-ray diffraction apparatus according to claim 6, wherein
   the X-ray measurement system is at least one of a rocking curve measuring device, a reflectometry device, a reciprocal lattice mapping device, an in-plane measuring device, and an X-ray powder diffraction apparatus.

8. The X-ray diffraction apparatus according to claim 7, wherein
   the X-ray topography means and the X-ray measurement system have a common X-ray source.

9. The X-ray diffraction apparatus according to claim 1, wherein
   the X-ray topography means has a semiconductor image sensor in which a plurality of semiconductor X-ray light-receiving circuit elements are lined up in a planar or linear formation.

10. The X-ray diffraction apparatus according to claim 1, wherein
    the sample is an optically transparent single crystal substance, surface of which reflects light of small amount.

11. The X-ray diffraction apparatus according to claim 1, further comprising:
    an X-ray measurement system for irradiating the sample with an X-ray within a narrower region than the region in which the sample is irradiated with an X-ray in the X-ray topography means, and detecting an X-ray exiting from the sample at this time; and
    sample moving means for causing the sample to perform a translational movement.

12. The X-ray diffraction apparatus according to claim 11, wherein the X-ray measurement system is at least one of a rocking curve measuring device, a reflectometry device, a reciprocal lattice mapping device, an in-plane measuring device, and an X-ray powder diffraction apparatus.

13. An X-ray diffraction measurement method for performing a measurement using the X-ray diffraction apparatus according to claim 12, the X-ray diffraction measurement method comprising:
   determining the presence of a crystal defect on the basis of an output result from the X-ray topography means;
   specifying the position of the crystal defect by the planar positional information on the basis of the synthesized video data determined by the video synthesis means;
   moving the sample by the sample moving means on the basis of the specified planar positional information, and causing the crystal defect to move to an X-ray irradiation position in the X-ray measurement system; and
   performing measurement by the X-ray measurement system.

14. The X-ray diffraction apparatus according to claim 11, wherein
   the X-ray topography means and the X-ray measurement system have a common X-ray source.

15. An X-ray diffraction measurement method for performing a measurement using the X-ray diffraction apparatus according to claim 14, the X-ray diffraction measurement method comprising:
   determining the presence of a crystal defect on the basis of an output result from the X-ray topography means;
   specifying the position of the crystal defect by the planar positional information on the basis of the synthesized video data determined by the video synthesis means;
   moving the sample by the sample moving means on the basis of the specified planar positional information, and causing the crystal defect to move to an X-ray irradiation position in the X-ray measurement system; and
   performing measurement by the X-ray measurement system.

16. An X-ray diffraction measurement method for performing a measurement using the X-ray diffraction apparatus according to claim 11, the X-ray diffraction measurement method comprising:
   determining the presence of a crystal defect on the basis of an output result from the X-ray topography means;
   specifying the position of the crystal defect by the planar positional information on the basis of the synthesized video data determined by the video synthesis means;
   moving the sample by the sample moving means on the basis of the specified planar positional information, and causing the crystal defect to move to an X-ray irradiation position in the X-ray measurement system; and
   performing measurement by the X-ray measurement system.

* * * * *